US005411706A

United States Patent [19]
Hubbard et al.

[11] Patent Number: 5,411,706
[45] Date of Patent: May 2, 1995

[54] PUMP/OXYGENATOR WITH BLOOD RECIRCULATION

[76] Inventors: Lloyd C. Hubbard, 20645 Bayview Ct., Excelsior, Minn. 55331; Earl W. Clausen, 16489 Ellerdale La., Eden Prairie, Minn. 55346

[21] Appl. No.: 193,736

[22] Filed: Feb. 9, 1994

[51] Int. Cl.⁶ ............... A61M 1/18; B01D 19/00; B01D 61/00
[52] U.S. Cl. .................. 422/46; 422/48; 210/321.75; 210/651; 417/423.14; 435/2
[58] Field of Search .................. 422/45, 46, 48; 210/651, 321.75; 417/423.14; 128/DIG. 3; 435/2

[56] References Cited

U.S. PATENT DOCUMENTS

| | | | |
|---|---|---|---|
| 3,890,969 | 6/1975 | Fischel | 128/214 R |
| 3,927,980 | 12/1975 | Leonard | 422/46 |
| 3,960,657 | 6/1976 | Bowley | 195/1.8 |
| 4,080,958 | 3/1978 | Bergman et al. | 128/1 |
| 4,828,543 | 5/1989 | Weiss et a. | 604/4 |
| 4,936,759 | 6/1990 | Clausen et al. | 417/423.14 |
| 5,270,005 | 12/1993 | Raible | 422/46 |
| 5,300,015 | 4/1994 | Runge | 600/16 |

*Primary Examiner*—Robert J. Warden
*Assistant Examiner*—N. Bhat
*Attorney, Agent, or Firm*—Kinney & Lange

[57] ABSTRACT

A system of processing blood during a surgical procedure includes a centrifugal blood pump with an inlet and an outlet, a means for oxygenating the blood and a means for recirculating a portion of the oxygenated blood to the inlet of the blood pump. The volume of blood recirculated through the system can be controlled by a flow control means. Recirculation of a portion of the blood reduces the cost and size of the system.

12 Claims, 3 Drawing Sheets

PUMP/OXYGENATOR WITH BLOOD RECIRCULATION

BACKGROUND OF THE INVENTION

The present invention relates to "heart/lung" machines used during surgical procedures. More particularly, the present invention relates to the recirculation of blood through the heart/lung machine enabling the use of smaller blood oxygenator and/or heat exchange elements.

Delicate surgical procedures require that the site of surgery remain motionless during the surgical process. This requirement made early heart surgery almost impossible, as stoppage of the heart's pumping action for the required length of time would invariably be fatal.

During the 1960's, prolonged non-fatal stoppage of the heart became possible by use of newly developed heart/lung machines. These machines consisted of a mechanical (i.e., first pumps were roller type) blood pump combined with a blood oxygenator. The heart/lung machines were capable of taking over the function of the natural heart and lungs for several hours and thus, enabling the development of techniques leading to today's extensive practice of open heart surgery.

Typically, centrifugal blood pumps derive their pumping action from the rotation of an impeller within a pumping chamber. Pump pressure is controlled by the rotational speed of the impeller. Centrifugal blood pumps are widely recognized as a safe, reliable, mechanical alternative to the roller pump. Although centrifugal blood pumps have a wide range of capacities, all pumps deliver enough blood to sustain a patient during surgery. An oxygenator is used to provide oxygenation of the blood during surgery. The oxygenator is the substitute for the natural lungs. Most currently used oxygenators employ a membrane made of a "microporous fiber bundle". A microporous fiber bundle is a collection of fine, hollow, porous polymer fibers which remove carbon dioxide and transfer oxygen to the blood coming into contact with the fiber bundle. Oxygenation of the blood and removal of carbon dioxide typically occurs when blood is passed over the outside of the fibers, while oxygen passes through the inside of the fibers. The amount of fibers which make up the fiber bundle must be sufficient to accomplish adequate gas transfer during the time that the blood is in contact with the oxygenator. Conventional heart/lung machines also utilize a heat exchanger, as well as a membrane oxygenator and a blood pump, to control the temperature of the patient during and after the surgical process.

SUMMARY OF THE INVENTION

By far, the most costly component of the oxygenator is the microporous fiber bundle which accomplishes gas transfer. The present invention takes advantage of the high flow capacity of conventional centrifugal blood pumps to use a smaller microporous fiber bundle in the oxygenator. A centrifugal blood pump is capable of outputting more blood than is needed by the patient during surgery.

The high rate of flow of the blood through the centrifugal blood pump allows the blood to pass over the microporous fiber bundle of the oxygenator multiple times via a recirculation line. By recirculating the blood through the oxygenator a number of times, the blood passes over the fiber bundle at a higher rate of flow than that being delivered to the patient. Adequate gas transfer occurs because the decreased size of the oxygenator is compensated by the blood passing over the oxygenator more than once. The amount of recirculation can be adjusted with a clamp on the recirculation line. If the recirculated blood is also passed over a heat exchanger multiple times, heat exchange is amplified so that a smaller heat exchanger can also be used.

DETAILED DESCRIPTION OF THE PREFERRED EMBODIMENTS

Figure 1:
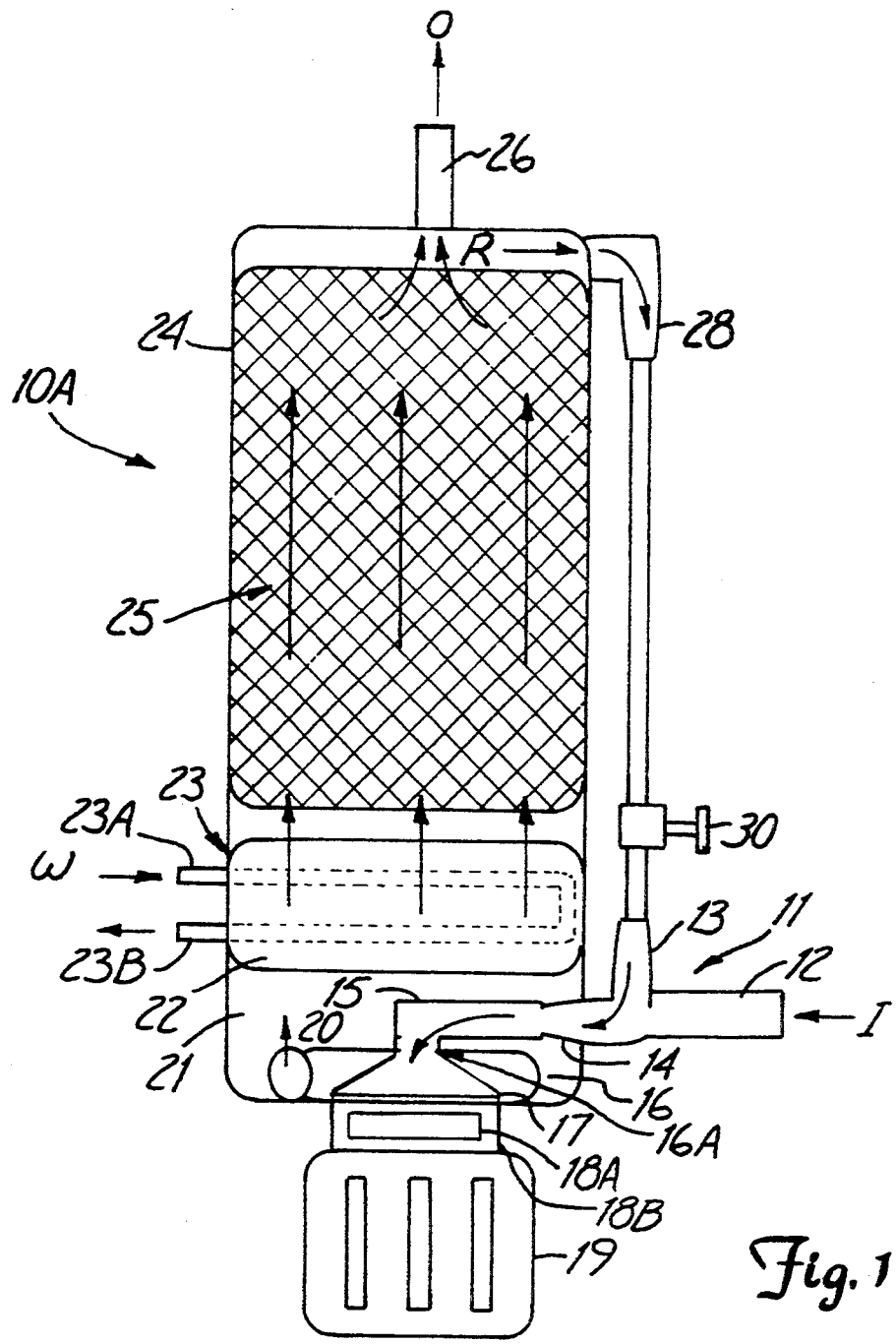
FIG. 1 shows a heart/lung machine with recirculation over the oxygenator and heat exchanger.
Figure 2:
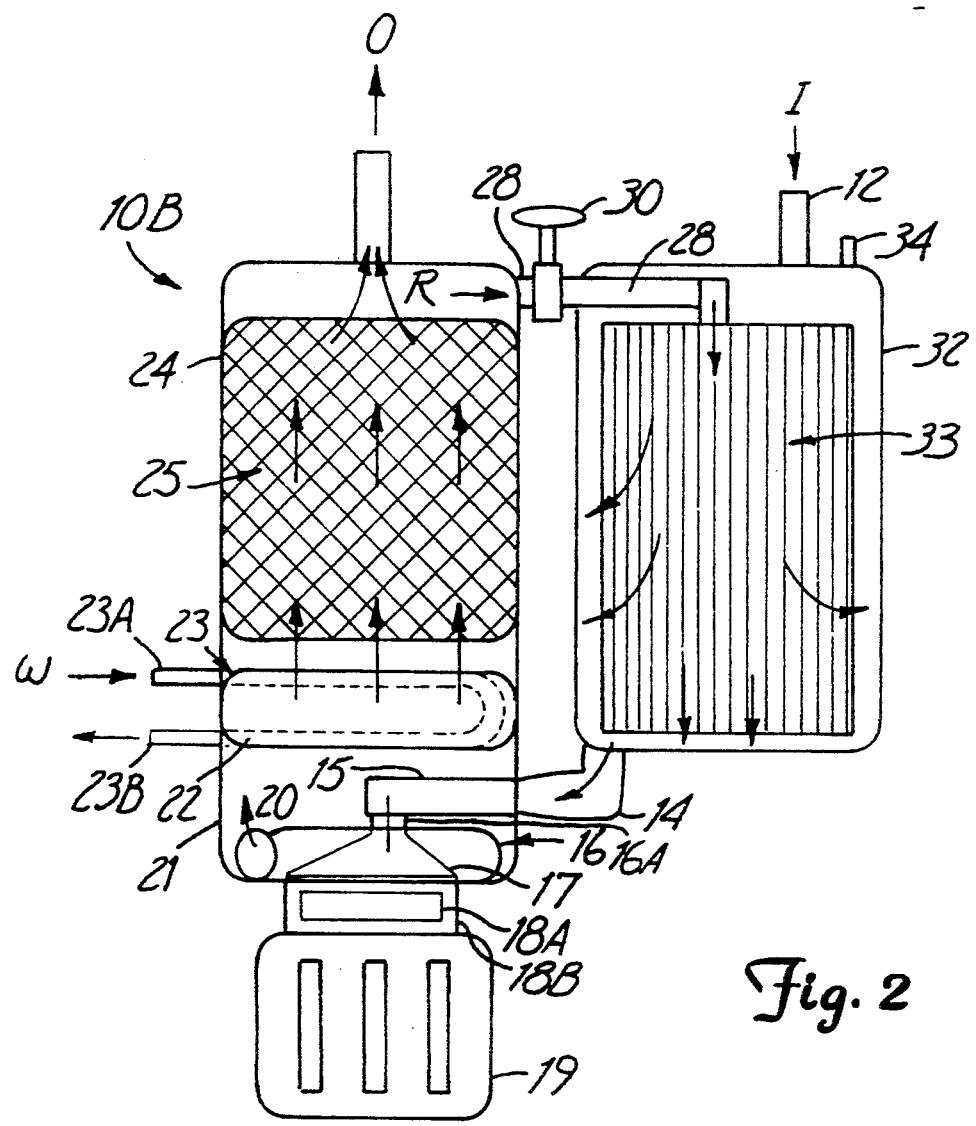
FIG. 2 shows an open reservoir heart/lung machine with recirculation over the oxygenator and heat exchanger.
Figure 3:
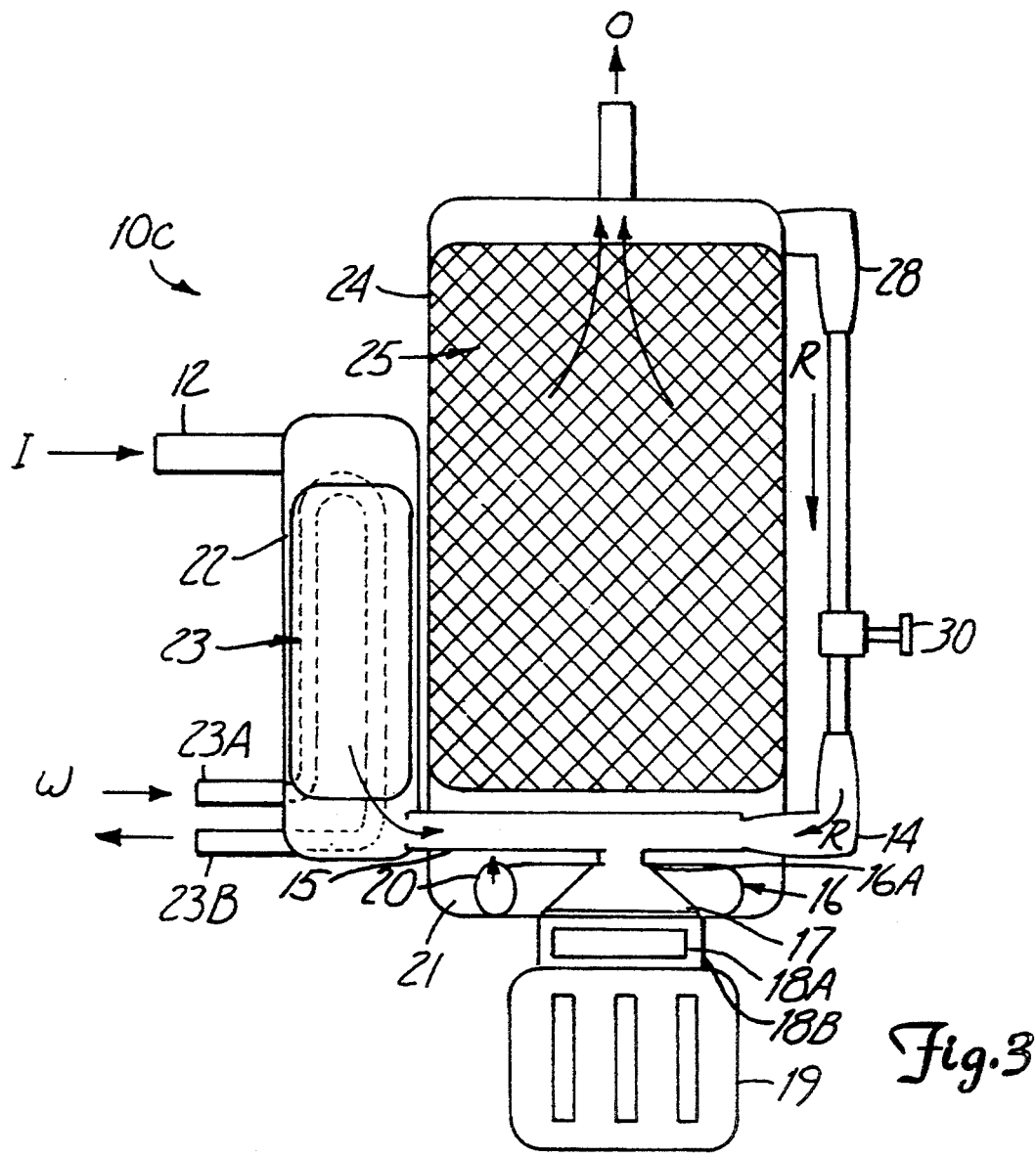
FIG. 3 shows a heart/lung machine with recirculation over the oxygenator element only.

FIGS. 1–3 show heart/lung machines 10A, 10B and 10C, respectively, including blood flow inlet 12, tube segments 14 and 15, centrifugal blood pump 16, blood pump inlet 16A, impeller 17, rotor 18A, magnetic coupling 18B, pump drive motor 19, blood pump outlet 20, holding chamber 21, heat exchanger 22, metal tubing 23, water inlet tube 23A, water outlet tube 23B, oxygenator 24, microporous fibers 25, blood flow outlet 26, recirculation line 28 and clamp 30. Incoming blood from the patient flows in the direction denoted by arrow I. Processed blood flowing out of the system is denoted by arrow O. Blood to be recirculated (i.e. recirculation blood) flows back into the system in a direction indicated by arrow R. Water flow into and out of heat exchanger 22 is indicated by arrow W. Three separate embodiments of the present invention are described in detail below.

1. Operation of the First Embodiment

FIG. 1 shows heart/lung machine 10A with recirculation through centrifugal blood pump 16, heat exchanger 22 and oxygenator 24. System 10A is compatible with a closed reservoir system. In a closed reservoir system, blood retrieved from the patient is held in an air tight reservoir (not shown).

In system 10A, blood from the patient enters T-connector 11 which includes tube segments 12, 13, 14 and 15. More particularly, blood enters inlet tube 12, flows through tube segments 14 and 15 and enters centrifugal blood pump 16 through blood pump inlet 16A. Tube segment 15 is attached to blood pump inlet 16A. The entering blood contacts impeller 17 of pump 16 and is circulated. Centrifugal blood pump 16 is magnetically driven by a source of rotation which is external to the pump. Specifically, impeller 17 of centrifugal pump 16 carries magnets which are coupled to magnets carried by rotor 18A within magnetic coupling 18B. Rotor 18A is driven by electric pump drive motor 19. Magnets of impeller 17 and rotor 18A rotate about the same axis of rotation. Impeller 17 rotates at the same speed as rotor 18A to circulate the blood in pump 16. Circulated blood is expelled from centrifugal blood pump 16 through blood pump outlet 20. The pumped blood is expelled from outlet 20 and enters holding chamber 21. When holding chamber 21 reaches its capacity, excess blood overflows into heat exchanger 22.

A heat exchanger is commonly used with oxygenators to facilitate cooling of the patient during surgery and warming of the patient following surgery. Heat exchanger 22 includes metal tubing 23 which is coated with blood compatible material so that blood may flow over the tubing. Circulating water flows within metal tubing 23 in the direction indicated by arrow W. Water enters heat exchanger 22 through inlet tube 23A and exits through outlet tube 23B. Metal tubing 23 is responsive to the temperature of the water, so as to warm or cool the blood as it passes through heat exchanger 22. In this manner, blood temperature is raised or lowered.

After passing over metal tubing 23 of heat exchanger 22, blood flows into oxygenator 24. Oxygenator 24 includes microporous fibers 25 which accomplish gas transfer. The blood enters oxygenator 24 and flows over the exterior of fibers 25. Air or oxygen flows within the interior of fibers 25. Gas transfer between the blood passing over the outside of fibers 25 and the oxygen flowing through the inside of the fibers occurs. Specifically, carbon dioxide is removed and oxygen is supplied to the blood.

A portion of the oxygenated blood then flows out of heart/lung machine 10A via outlet 26 in the direction indicated by arrow 0. Another portion of the blood, however, is recirculated. Recirculation blood flows in the direction indicated by arrow R and enters recirculation line 28. Blood travels down recirculation line 28, through tube segment 13 of T-connector 11 and intermixes with the incoming blood in inlet tube 12. Together with the blood coming from the patient, the recirculation blood flows toward blood pump inlet 16A of centrifugal blood pump 16. The flow of blood through recirculating line 28 can be controlled by a flow control means, such as clamp 30. Clamp 30 can be rotated so as to obstruct the flow of blood in recirculation line 28 to control the amount of blood that flows into blood pump inlet 16A. The recirculated blood flows through pump 16 and over heat exchanger 22 and oxygenator 24 along with the incoming blood as described above. Thus, a portion of the blood is recirculated through heart/lung machine 10A before being outputted to the patient.

Recirculation of the blood increases the output capacity of the system and allows heat exchanger 22 and oxygenator 24 to be smaller than would ordinarily be required. Using the high flow rates of conventional centrifugal blood pump 16, a sufficient amount of oxygenated and temperature controlled blood can be generated to sustain an adult patient during the course of a surgery. The ratio of recirculation to incoming blood in the system at any given time is controlled by clamp 30. However, blood is commonly recirculated through the system at least twice before re-entering the patient. By controlling the amount of recirculation using clamp 30, the flow capacity of heart/lung machine 10A can be altered to serve patients of different sizes. The decreased size of oxygenator 24 and heat exchanger 22 results in a less expensive, more integrated heart/lung machine.

2. Operation of the Second Embodiment

FIG. 2 shows open reservoir heart/lung machine 10B with recirculation over heat exchanger 22 and oxygenator 24. An open reservoir system accumulates blood from the patient in a reservoir which is open to the atmosphere. The operator of the heart/lung machine (i.e., the perfusionist) must constantly monitor the system to insure that the capacity of the reservoir is not exceeded.

In system 10B, blood is siphoned from the patient and enters the system through inlet tube 12. Reservoir 32 receives incoming blood from inlet tube 12. Reservoir 32 is supplied with vent 34 so that air contained within the reservoir can escape as the blood enters. Reservoir 32 includes filter 33 to eliminate debris in the blood before it flows to centrifugal blood pump 16. Blood passes through reservoir 32 and flows through tube segments 14 and 15 to enter centrifugal blood pump 16 through blood pump inlet 16A. Tube segment 15 is attached to blood pump inlet 16A. Centrifugal blood pump 16 is magnetically driven in the same manner as the first embodiment. Similar to the first embodiment, as the blood enters pump 16, it contacts impeller 17 and is circulated. The circulated blood is then expelled from pump 16 via blood pump outlet 20. The expelled blood enters holding chamber 21. When holding chamber 21 reaches its capacity, the blood from chamber 21 overflows into heat exchanger 22. The temperature of the blood is regulated by heat exchanger 22 in the same manner as described in the first embodiment.

After passing over heat exchanger 22, the blood enters oxygenator 24. The blood in oxygenator 24 flows over the exterior of microporous fibers 25. As the blood flows over fibers 25, carbon dioxide is removed from the blood and oxygen is supplied to the blood. After passing through oxygenator 24, a portion of the oxygenated, temperature controlled blood flows out of heart/lung system 10B through outlet 26 and returns to the patient. Another portion of the blood, however, is recirculated through system 10B. Blood which did not exit the system through outlet 26 enters recirculation line 28. The recirculation blood travels through recirculation line 28 and re-enters reservoir 32. The flow of blood entering reservoir 32 can be controlled by clamp 30. More particularly, clamp 30 can be rotated so as to obstruct the flow of blood within recirculation line 28, so as to control the amount of blood which ultimately flows to blood pump inlet 16A. The recirculation blood intermixes with incoming blood from the patient in reservoir 32. Along with the incoming blood, the recirculation blood circulates through centrifugal blood pump 16, heat exchanger 22 and oxygenator element 24 of system 10B in the manner described above.

3. Operation of the Third Embodiment

FIG. 3 shows closed reservoir heart/lung machine 10C with recirculation over oxygenator element 24 only. Similar to the closed reservoir system described in FIG. 1, blood is siphoned from the patient and held in a closed reservoir (not shown) until it is processed by heart/lung machine 10C.

In system 10C, blood from the patient enters heat exchanger 22 through blood flow inlet 12. The temperature controlled blood is expelled from heat exchanger 22 and enters tube segment 15. Tube segment 15 is connected to blood pump inlet 16A of centrifugal blood pump 16. Blood from tube segment 15 flows into blood pump inlet 16A. Once it enters centrifugal blood pump 16, the blood is circulated in the same manner described in the first and second embodiments. The blood from pump 16 is expelled from outlet 20. The expelled blood enters holding chamber 21. When holding chamber 21 reaches its capacity, blood flows into oxygenator 24.

Oxygenator element 24 includes microporous fibers 25. As blood enters oxygenator 24, it flows over fibers 25. Carbon dioxide is exchanged for oxygen while the blood is passing over the exterior of the fibers as described in the prior embodiments.

A portion of the oxygenated, temperature controlled blood then exits heart/lung system 10C through outlet 26, and returns to the patient. Another portion of the blood, however, enters recirculation line 28. The recirculation blood travels down recirculation line 28, through tube segment 14 and re-enters tube segment 15. Blood entering tube segment 15 from recirculation line 28 mixes with the incoming blood from heat exchanger 22 when entering blood pump inlet 16A. The flow of blood from recirculation line 28 entering blood pump inlet 16A can be controlled by clamp 30 which is positioned on recirculation line 28. Clamp 30 can be rotated as to obstruct the flow of blood in recirculation line 28 so as to control the amount of recirculation blood entering tube segment 15.

The blood from recirculation line 28 and the incoming blood enter centrifugal blood pump 16 and flow over oxygenator 24 as described above. Thus, a portion of the blood is recirculated through the oxygenator 24 of heart/lung machine 10C before being outputted to the patient. There is no recirculation over heat exchanger 22 in this embodiment.

Significant advantages accrue by utilizing the high flow capacity of the centrifugal blood pump as an integral part of the heart/lung machine. Cost is reduced because less microporous fibers are needed. Further, a smaller sized package of centrifugal blood pump, oxygenator, and/or heat exchanger results in increased convenience to the surgical team.

Although the present invention has been described with reference to preferred embodiments, workers skilled in the art will recognize that changes may be made in form and detail without departing from the spirit and scope of the invention.

What is claimed is:

1. A system for processing blood during a surgical procedure comprising:
    a system inlet for receiving blood;
    a system outlet for delivering blood;
    a blood pump for circulating blood received at the system inlet under pressure to the system outlet., the blood pump having an inlet connected to the system inlet through which blood is supplied to the blood pump and a pump outlet through which blood is expelled from the blood pump;
    means for oxygenating the blood expelled from the outlet of the blood pump, wherein the means for oxygenating the blood is connected to the system outlet to supply a first portion of oxygenated blood to the system outlet; and
    means for recirculating a second portion of the oxygenated blood from the means for oxygenating to the pump inlet of the blood pump.

2. The system of claim 1 wherein the means for recirculating blood to the inlet of the pump comprises:
    a recirculation line coupled between the oxygenating means and the inlet of the blood pump.

3. The system of claim 2 and further comprising a flow control means to regulate blood flow to the inlet of the blood pump.

4. The system of claim 1 and further comprising means for controlling blood temperature during a surgical procedure.

5. The system of claim 4 wherein the means for controlling blood temperature is coupled between the blood pump and the oxygenating means.

6. The system of claim 4 wherein the means for controlling blood temperature is coupled to the blood pump.

7. A method of processing blood through a system during a surgical procedure comprising:
    receiving blood through a system inlet;
    supplying blood to a blood pump for circulating blood received at the system inlet under pressure to a system outlet wherein the blood pump has a pump inlet connected to the system inlet for receiving blood and a pump outlet for expelling blood;
    oxygenating blood expelled from the pump outlet of the blood pump, wherein the means for oxygenating the blood is connected to a system outlet to supply a first portion of oxygenated blood to the system outlet; and
    recirculating a second portion of the oxygenated blood to the pump inlet of the blood pump.

8. The method of claim 7 wherein oxygenating blood expelled from the outlet of the blood pump further comprises:
    receiving blood from a holding chamber coupled between the outlet of the blood pump and the means for oxygenating the blood; and
    passing the blood received from the holding chamber over microporous fibers.

9. The method of claim 7 wherein recirculating a portion of the oxygenated blood to the inlet of the blood pump further comprises:
    attaching a recirculation line coupled between the oxygenating means and the blood pump.

10. The method of claim 9 and further comprising:
    controlling blood flow in the recirculation line so that the blood entering the inlet of the blood pump through the recirculation line may be regulated.

11. The method of claim 7 and further comprising:
    controlling blood temperature.

12. The method of claim 10 wherein controlling blood temperature comprises passing the blood over an exterior of blood compatible metal tubing wherein temperature controlled water flows within an interior of the metal tubing.

* * * * *